United States Patent
Thomas et al.

(10) Patent No.: US 9,554,772 B2
(45) Date of Patent: Jan. 31, 2017

(54) NON-INVASIVE IMAGER FOR MEDICAL APPLICATIONS

(71) Applicants: Mammen Thomas, Hercules, CA (US); Arun Mammen Thomas, Dublin, CA (US)

(72) Inventors: Mammen Thomas, Hercules, CA (US); Arun Mammen Thomas, Dublin, CA (US)

( * ) Notice: Subject to any disclaimer, the term of this patent is extended or adjusted under 35 U.S.C. 154(b) by 193 days.

(21) Appl. No.: 14/198,498

(22) Filed: Mar. 5, 2014

(65) Prior Publication Data

US 2015/0250450 A1 Sep. 10, 2015

(51) Int. Cl.
| | |
|---|---|
| *A61B 5/05* | (2006.01) |
| *A61B 8/00* | (2006.01) |
| *A61B 5/055* | (2006.01) |
| *A61B 5/00* | (2006.01) |
| *A61B 8/08* | (2006.01) |
| *A61B 5/06* | (2006.01) |

(52) U.S. Cl.
CPC .............. *A61B 8/4416* (2013.01); *A61B 5/055* (2013.01); *A61B 5/7425* (2013.01); *A61B 8/085* (2013.01); *A61B 8/0841* (2013.01); *A61B 5/062* (2013.01); *A61B 8/483* (2013.01); *A61B 2090/364* (2016.02); *A61B 2090/367* (2016.02)

(58) Field of Classification Search
CPC ..... A61B 19/5244; A61B 5/055; A61B 5/062; A61B 5/7425; A61B 8/4416; A61B 8/0841; A61B 8/085; A61B 2090/364; A61B 2090/367; A61B 8/483

See application file for complete search history.

(56) References Cited

U.S. PATENT DOCUMENTS

| | | | | |
|---|---|---|---|---|
| 2013/0053679 | A1* | 2/2013 | Owen | A61B 6/5247 600/411 |
| 2013/0322717 | A1* | 12/2013 | Bar-Shalev | G06T 7/0044 382/131 |
| 2013/0322722 | A1* | 12/2013 | Vija | G06F 19/321 382/131 |
| 2014/0347051 | A1* | 11/2014 | Kecskemeti | G01R 33/5602 324/309 |

* cited by examiner

*Primary Examiner* — Sanjay Cattungal

(57) ABSTRACT

A method and process is described for providing Non-Invasive three dimensional (3-D) image of a patient such that during surgical or other procedures, the person performing the procedure can visually identify the organs and the location of the instruments in real time inside the body. Such a non-invasive imaging and reconstruction using spatially coordinated imaging in three dimensions is a very valuable tool especially to the surgical community. The high powered computing capabilities, advances in the imaging techniques, individually or in combination when combined with noise filtering and error correction capabilities, have made accurate 3-D imaging in real time from scans a reality. These 3-D images are also used as a diagnostic tool, a practice tool and a teaching tool by the medical community. There may be other applications in these and related areas which may emerge as technology develops and they become apparent to individuals practicing the art.

10 Claims, 2 Drawing Sheets

NON-INVASIVE IMAGER FOR MEDICAL APPLICATIONS

FIELD OF INVENTION

Figure 1:
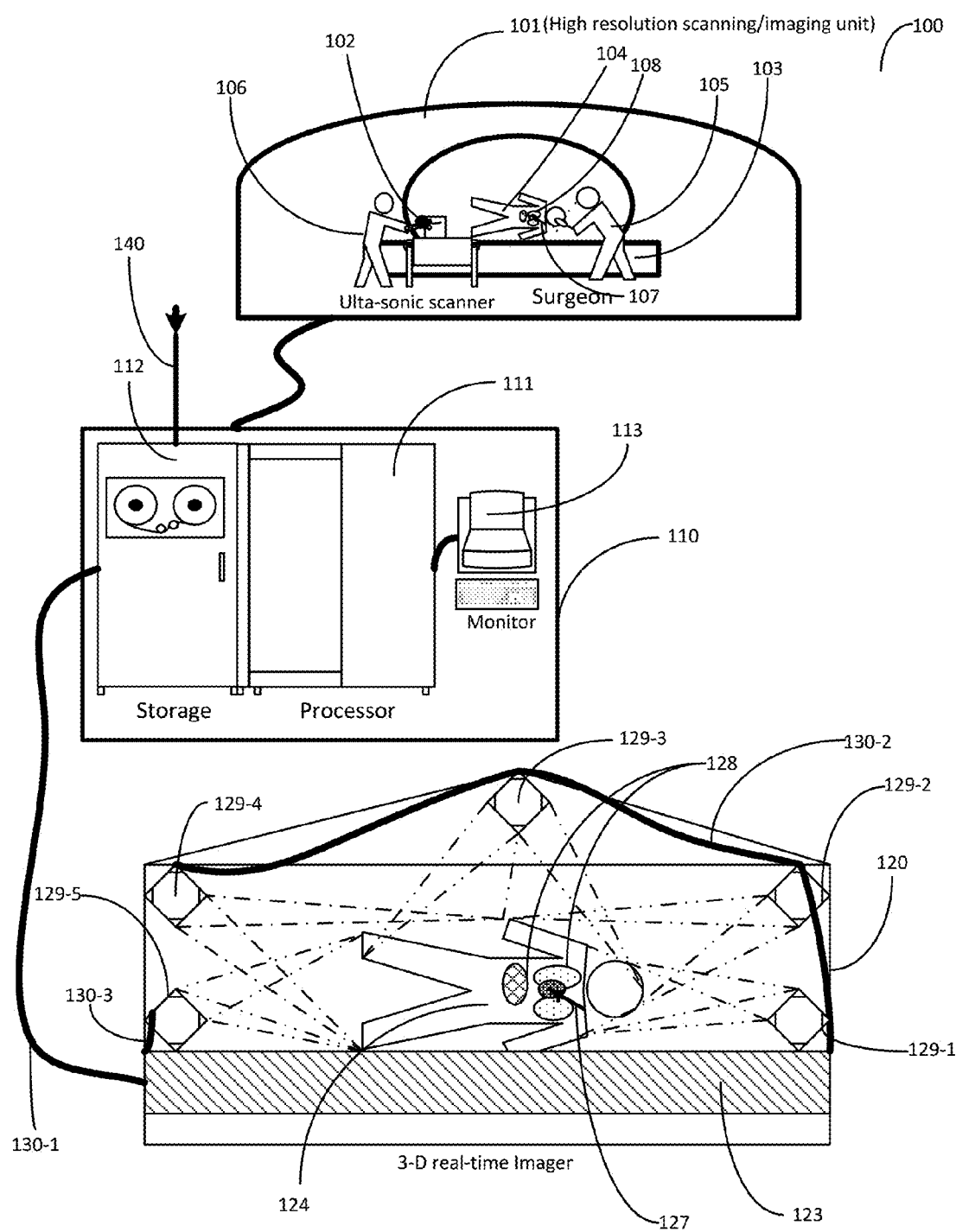

This invention addresses the need of the medical and veterinary community to visualize in real time and in three dimensions, the field of operation and the location of instruments during procedures and also accurate placement of medicines.

DESCRIPTION OF BACKGROUND OF THE INVENTION

Today most of the robot assisted procedures are conducted by the surgeon operating with a limited vision of the operating field, through microscopes and manipulating the instruments by what is visible in the narrow field of view through the optical cable inserted into the body with the surgical instrumentation. The surgeon has no real wide view of the operating area. There has been scanning and imaging technology such as magnetic resonance imaging (MRI), computed tomography (CT), X-ray, ultra-sound (ultrasonic imaging) etc. which are in wide spread use in diagnostic fields. 3-D imaging technology is also available today, to a limited extend using the images generated which are being used for diagnostic and training purposes. This has improved the capabilities existing for practice of nano-surgery and micro-surgery or procedure (key-hole procedures) and made them more prevalent. But as of now there are no capabilities for viewing the surgery or procedure in a 3-D image projection where the individual doing the procedure can visually see what is being done in real time in a simulated environment. Such a capability if available will be very useful to improve the efficiency of procedures and reduce the problems substantially for key-hole procedures. The MRI scanning and CT scanning are all techniques used today for diagnostic purposes. These are both high resolution scanning methods. These high resolution scanning and processing of the scanned data to generate usable information and images are slow and not real time. The images need to be reconstructed by mathematical computation which makes it a good and reliable diagnostic tool but not easily usable in real time procedures or consultations during the procedures. They are also not usable in procedures to see the location of the instruments inside the body as the procedures happen. This makes them not suitable, by themselves, for the applications which are covered by the current invention.

Low intensity X-ray and Ultra-Sonic scanning to generate images are the other two modes of imaging in use in the medical field that provide fast images but with somewhat lower resolution. All these techniques are in use today as stand-alone applications. It will be of use if a system and method can be found that provide real time visual imaging capability with spatial coordination, such that 3-D images can be generated and updated in real time for conducting procedures with full visibility to the field of the procedure and instrument placement as the procedure is conducted. Such a spatially coordinated 3-D image will also enhance the capability to provide automated robotic implementation of procedures.

What is needed and is proposed hence is the use of ultra-sonic and low level X-ray imaging techniques, that are fast imaging techniques providing real time imaging capability, enabled for use in conjunction with high resolution scanning techniques that provide clear high resolution imaging capabilities, such as MRI or CT, to enable generation of spatially aligned real time continuously updating 3-D image of the patient, thereby providing enhanced real-time visual capability for critical procedures. This is a new field which the inventors believe is an emerging field.

SUMMARY OF INVENTION

The present invention is aimed at providing the medical and veterinary community tools to conduct invasive procedures with visibility and control using spatially aligned holographic imaging in real-time for guidance of tools and placement of medicines while enabling real-time viewing and follow-up by the surgical team and experts during the procedure itself. The invention is also an enabler using the 3-D image for improving the diagnosis of problems, improving the capability to do remote consultation with experts in the field, thereby reducing the cost and improving success rate of procedures. This invention also provides the capability to practice procedures outside of the body on the 3D image of the actual individual, prior to start of procedure, so that the team becomes familiar with the procedure and the nature of the individual before starting the procedure, thereby reducing the risk factor.

The present invention enable the combining of data from multiple scanning systems/imaging systems, using pre-defined fixed points as reference to generate and update image data to provide the capability for generating real time 3-D image of an object or a person within the field of the scans.

Computed Tomography (CT) scan that use either X-rays or Gamma rays, and standard X-ray imaging, though much have improved over the past years to provide good images using lower radiation levels, still damage the tissues due to accumulated radiation dosage. They are capable of low distortion images and deeper penetration through bones and underlying tissues. Magnetic resonance imaging (MRI) using magnetic resonance scanning techniques are also very accurate and can produce accurate and detailed images of the human body sections. These high resolution scans require mathematical computations that take time and hence cannot be done in real-time. MRI also limits the use of instruments that are made with certain metals that are magnetic, which also limit its use in real time procedures. All these scanning methods are used today for support and verification of diagnosis. 3-D images can be generated from these scans but these scanning and subsequent imaging techniques are not suitable at present for continuous real-time monitoring and display of the field of procedure. (Though in future we can expect the x-ray sensitivity to be increased for detection, making very high resolution images possible with very low dose X-ray radiation, thereby making x-rays and CT scans viable tools for real-time image generation. Time limitations for computation of image from MRIs and CT scans are also expected to change with the increased speed of computing systems enabling computational capabilities for generating 3-D images, such as holographic images, in future). Ultra-Sound scanning and imaging currently has poorer image definition but does not cause permanent harm to the tissues due to exposure to harmful radiation and is a good tool to identify soft tissue regions within the body. It also has no limitation on use of metallic tools within its range for procedures. Hence a combination of the initial scanning using a high resolution scanning systems, with real time updating of the 3-D display for monitoring by ultra-sound (ultra-sonic scanning) will provide the best choice for generation of real time 3-D image generation, such as a hologram today. Ultra-sound scanning is the scan of choice for continuous imaging during procedures as it stands today, as described in one embodiment of the invention.

In order to provide proper alignment between the multiple scanning techniques for 3-D imaging, a set of accurate alignment points need to be defined in the three dimensions, enclosing the field of the patient which will remain constant and enable other reference points to be generated around the field of the procedure that reference the fixed alignment points. The set of alignment points enable the scan data from different scans to be combined using the reference points to eliminate displacement errors when combining and updating 3-D images generated and displayed. The preference is to have fixed alignment points that are stationary, such as on the table used for patient positioning, but alignment points and acoustic registration points can also be defined on or around, including under the person after the person has been sedated, which may be correlated to the fixed alignment points if needed.

Ultra-sonic imaging is a non-invasive technique that can be used to generate the over all image of the field of operation. This imaging method is very useful in soft tissue areas. This imaging technique does not have long term harmful effects that the X-ray imaging has, hence it is preferable to use Ultra-sonic imaging for continuous real-time updated display including 3-D display, for monitoring during any procedure, with initial accurate high resolution imaging support from, MRI, CT, X-ray or other imaging technologies to develop a complete 3D Imaging such as holographic imaging of the field of interest for diagnostic imaging and planning purposes as well as tracking and implementation of minimally invasive procedures preferably using robotics.

These scans produced are combined and converted to image data enabled to produce a combined 3-D image data enabled to produce a 3-D image of the patient and the field of the procedure. The 3-D image date produced is suitable for generating a 3D image similar to a three dimensional hologram. The combining and processing of the scan data to produce the 3-D image data is by using the processing power of a dedicated image processing system. The 3-D image data produced and updated in real time is provided to a 3-D image generator (such as a set of projection devices) that generate a real time 3-D image, using any of the available imaging techniques such as a three dimensional hologram, of the patient. The real time 3-D image generated will provide the capability to view the subject at differing magnifications, and from differing orientations by image manipulation as needed, without affecting the spatial coordination and linkage established to the patient, to enable complete viewing of the procedure and increase the accuracy of the procedure. The 3-D image thereby allows the surgical team a virtual view of the operating field, in real time, during implementation of the procedure and to and display the actions as it happens. Though during diagnostic and planning/practice stages the 3-D image can be used as an isolated training entity, during procedure itself the image is placed in controlled spatial relationship to the patient under sedation for active and real-timing and displaying of the procedure, with guided placement of instrumentation, for the procedure and feeding of medication, using updates from the continuous monitoring scanners, typically ultra-sonic scanners placed critically at spatially defined locations, to allow the complete 3-D view of the field of the procedure.

The generation and use of the holographic imaging capability allows the formation of a 3-D image which may be a three dimensional holographic picture, in real time, for complete understanding and planning of the procedure ahead of time using the individual as subject. This will reduce the time the patient has to be worked on and also provide for pre-planning of possible complications before the procedure, making for higher safety and faster recovery. The images produced and displayed during the procedure itself will be spatially associated with the patient and show the location of the tissues and organs and the location of the instruments in a three dimensional real time relationship allowing for continuous updated display for monitoring and accurate execution of the procedure.

It should be noted that even though ultra-sonic scanners are the preferred continuous scanning and updating scanners of choice today, this can change as improvements in other scanner types are made or new combination scanners are developed which provide equal or better capabilities for the continuous and real time monitoring and display.

The use of formation of a spatially aligned 3-D image, with real time updating of the instrumentation and activities within the procedure field, provide for improved visibility, and accuracy of the procedure, while enabling monitoring, and feedback by observing or assisting experts to reduce problems, in real time during invasive or minimally invasive procedures, to reduce risk and trauma to the patient, is what is claimed by the inventors of the application.

OBJECTIVES AND ADVANTAGES OF THE DISCLOSURE

Some of the clear advantages of the applied concepts are:
1. Possible pre-planning and practicing of the procedure in a three dimensional holographic environment, on the individual who is being considered for a procedure, which is generated by the imaging technique.
2. Improved capability for diagnostic evaluation and consultation with experts at remote locations with full capability to view and study the problem and the suggested procedure on the individual.
3. Enable pre procedure practice of the procedure on the available spatially linked 3-D image to identify and get accustomed to the peculiarities and uniqueness of the individual and the procedure field.
4. Continuous three dimensional imaging of the procedure field providing real-time viewing and monitoring capability during procedure to see that there are no unidentified problem areas.
5. Better visibility of the field in which the procedure is taking place with specificity of location of the instruments and robotics used in the procedure field.
6. Capability to have remote procedures performed by experts, with out being present on location—using remote real time execution with monitoring using the 3-D display.
7. Capability to view the display to monitor and provide advice to the expert conducting the procedure in real time by other observing experts to help overcome difficulties.

EXPLANATION/DEFINITION OF TERMS

1. Scanning system and imaging system are used interchangeably.

DRAWING FIGURES

FIG. 1:—Is a typical block diagram of a system for achieving the 3-D image as per one embodiment of the invention.

Figure 2:
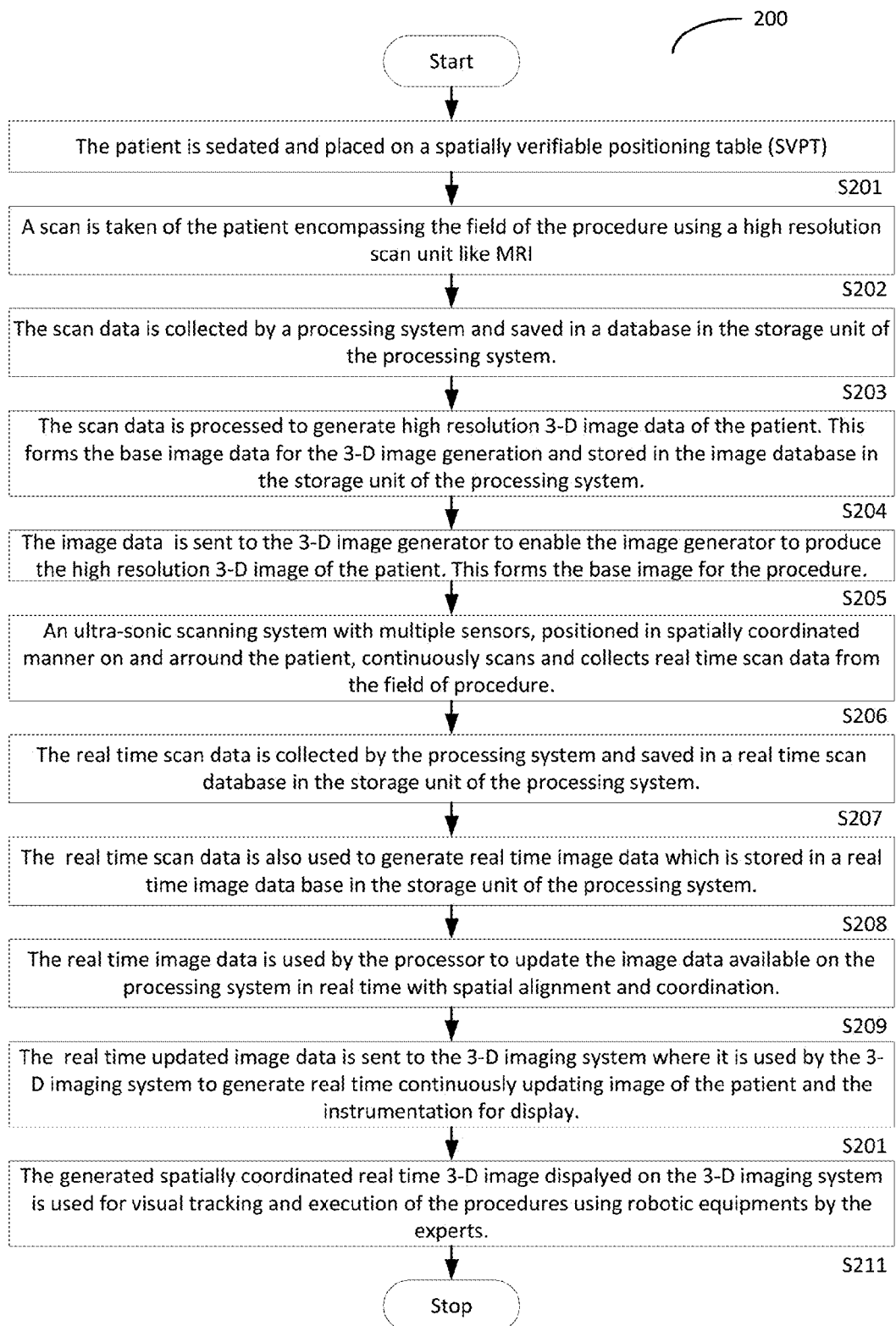

FIG. 2:—Is a flow chart of the use of the development of a spatially linked 3-D image for use in the procedure as per an embodiment of the invention.

DESCRIPTION OF THE INVENTION

A method and process is described for providing Non-Invasive3-D image (e.g. a three dimensional holographic image) of the patient in a spatially coordinated and updatable manner, such that during surgical or other procedures the person performing the procedure can visually identify the organs and the location of the instruments in real time inside the body. Hence a spatially aligned non-invasive imaging and reconstruction using any available 3-D image generator, such as a 3-D projector, generating a 3-D image of the patient, will be very valuable tool to the surgical community. The high powered computing capabilities, advances in the imaging techniques, individually or in combination, when combined with noise filtering and error correction capabilities, have made accurate 3-D imaging such as 3-D holograms from scans a reality. These 3-D images are usable as a diagnostic tool and implementation tool by the medical community. It can also be a valuable teaching tool. There may be other applications in medical and related areas which may emerge as the technology develops and new use cases become apparent to individuals practicing the art.

By using these spatially coordinated, real time, holographic or other available types of 3-D image during surgical or other procedures, the person performing the procedure can visually identify the organs and the location of the instruments in real time inside the body. The advances in the scanning techniques, such as X-ray, CT Scans, nuclear medical scans, MRI scans and Ultra sound, individually and in combination, improved noise filtering capabilities enable generation of accurate 3-D images such as 3-D holograms from these scans, using available high power, high speed processors for combining and manipulation of scan data. The medical community can use these types of 3-D images produced using any of the available 3D-image generators, as diagnostic tools and training tools. The 3-D images produced enable the capability for having expert consultants providing second opinions and advice over long distance by reviewing the 3-D images sent to them through internet or other data communication means. Nano/micro-Surgery, using robotics with visual coverage of the whole area of the surgery, unlike the limited view through a scope, is one of the area that benefits most by this invention. The real time visual capabilities provided by the 3-D image, spatially aligned to the patient, enable supervision and guidance of the location of robots in the wider field of the procedure within the body. This will provide accurate visual guidance to the instruments used for operations and placement of medicines within the human body to achieve best results. By using enlargement and magnification of the 3-D image, using capabilities provided by manipulation of the 3-D imaging data by the processing unit, the 3-D image, such as a 3-D holographic image, is able to provide better coverage of the area of the procedure so that the placement and movement of instruments can be more accurately done than when guiding them when looking through a scope with limited field of view.

The availability of a 3-D image, such as a holographic image, of the patient will also help the surgical team practice the operation outside the patient, before starting the procedure, so that there is reduced risk of failure. The diagnostic capability of such a technology will be substantial as experts can be sent the image over data links and they can visualize the operation and its ramifications, in real time, without being present on site and provide feedback to the surgeon performing the procedure in advance during planning stages as well as in real time during the procedure.

By combining high resolution scan data from scanners such as MRI, CT or X-ray with other suitable high speed real-time scanning techniques, such as ultra-sound, the formation of a real-time three dimensional holographic image spatially linked to the patient on the table, the doctors are able to determine in real-time where the instrumentation is and what need to be done to complete the procedure and where to place medication within the affected regions for maximizing its impact.

DETAILED DESCRIPTION OF INVENTION

FIG. 1 shows an exemplary and non-limiting system 100 for implementation of one embodiment of the invention.

The patient under sedation may be located on a spatially verifiable reference generation unit (SVRU), such as a positioning platform or positioning table (SVPT) 103. The SVRU provide fixed and accurate reference points and reference surfaces which allow fixing of additional reference points around the patient for convenience and accuracy, in reference to these fixed references. Using these references enable the location and position fixing of any items within the field to be always referenced and recognized with relation to the SVRU such as an SVPT 103. A SVRU, such as a SVPT 103, is essential for the implementation of the invention. These reference points in three dimensions are used for aligning and combining scan data from multiple scanning systems, such as the high resolution scans and real time scans to generate 3-D scan data that can be up used to generate the necessary real time image data for the 3-D image generation. The reference points are hence used to align the various scans used in the generation of the 3-D image in real time, such that the scan data from multiple systems are combined effectively and aligned to each other minimizing the displacement errors that can occur when using data from multiple sources.

A high resolution imaging unit 101, (also called a high resolution scanner) such as magnetic resonance imaging (MRI) or Computed Tomography (CT) imaging, is used to generate an accurate and high resolution scan of the patient, 104, (may be limited to the field of the procedure) under sedation. This high resolution scan data (HRSD) is coordinated spatially with the references provided by the SVPT 103 for providing spatial alignment to the generated 3-D image. A series of ultrasonic scanning heads, that can operate individually or in combination, from an ultra-sonic imager 102, (also called ultra-sonic scanner) are placed in accurately identified coordinate locations on or around the patient to provide full coverage of the field of procedure and be also spatially coordinated with the reference points provided by the SVPT 103. The ultra-sonic scanning tech. 106 using the ultra-sonic imager 102 generate continuous scans of the field of the procedure in real time during the procedure being conducted by the doctor 105 on the patient 104. The field of the procedure in FIG. 1 for clarity of example shows the location of organs 108 and instrumentation in place 107 within the field of the procedure which are not directly visible.

The high resolution imaging unit 101 and ultra-sonic imager 102 as well as the spatially verifiable positioning table (SVPT) 103 are linked to a high speed data and image processing system (processing system) 110 for collection and storage of the scan data for image processing and 3-D image data preparation. The processing system 110 comprise at least one processor 111, a storage unit 112, that has at least a program storage and multiple databases for data storage capabilities, and at least an input/output (IO) terminal 113, enabling data and program input and image viewing capabilities. The scan data from the high resolution imaging unit 101 is collected and stored in a high resolution scan database and the ultra-sonic scan is collected and stored in a real time scan database in the data storage unit 112.

The processing system 110 processes the spatially verifiable scan data generated by the high resolution imaging unit 101 to convert it to image data usable for generation of 3-D image, with spatial coordination and saves the image data in an image database in the data storage unit 112. The processing system 110 further uses the real time scan data from the ultra-sonic scanner 102 to generate updates in real time for the high resolution 3-D image data. The real time ultra-sonic data is also spatially coordinated with the patient and high resolution scan data using the reference points provided by the SVPT 103, enable the ultra-sonic scan updates to be fully coordinated and aligned spatially with the existing scan data stored in the and generate the necessary image data enabling continuous updates to the 3-D image data in real time. The real time scan data from the ultra-sonic sensors of the ultra-sonic imager, 102, hence enable real time modification of the image data as procedures happen. The real time image data generated by the processor 111 as updates to the 3-D image data are also stored in a real time image database in the data storage 112 and retained for analysis as historic data of the procedure. The real time scan data is used by the processor 111 to update and modify the 3-D image data on a continuous and real time basis. This updated image data is used for generation of the 3-D image of the embodiments of the invention.

The processing system 110 is linked to a 3-D image generator 120 such as a holographic projector or holographic image generator, for generating the 3-D image with spatial coordination to the patient, from the combined and up dated 3-D image data produced and manipulated for generation of the 3-D image projection, by the processor 111.

The 3-D imager or 3-D image generator 120, such as a holographic projector, may comprise at least a reference base 123 and multiple projectors 129-1 to 129-5. There is additional processing capability built into the 3-D image generator, 120, for data distribution and data manipulation. The updated image data generated by the processing system 110 is provided via data links 130-1 to 130-3 to the various projectors which working individually or together, depending on the type of imager used, enable the formation and display of the 3-D image of the patient 124 within the 3-D imager 120. The 3-D image of the patient 124 will provide detailed view of the patient 124 with internal organs 128 as generated from the scan data from the high resolution imaging unit 101 are combined with the real time scan inputs from the ultra-sonic imager 102, with spatial coordination and alignment to generate real time image data enabled to provide the view of the field of the procedure, instruments 127 being used and placement of these instruments with the field where the procedure is undertaken in real time.

The original high resolution scan data from the high resolution image unit 101 used to generate the image data for the 3-D imager 120 are hence updated using real time scan inputs from the ultra-sonic scanner 102 by the processing system 110, which combines the inputs in real time in a spatially coordinated fashion by referencing the coordinates of the SVPT 103 and placement of the ultrasound sensors. This real-time updated scan data is processed by the processing system 110 to continuously update the 3-D image data and generate real time 3-D image 124 of the patient with the procedure being conducted and the instrumentation used 127 to the doctor/surgeon and to the expert advisors.

By providing a communication capability 140 (either by Wi-Fi or wired) to the processing system 120 it is possible to send the 3-D image data to remote sites by internet or other communication means, for visual following of the procedure by off-site experts, who are then able to provide advice to the doctor 105 conducting the procedure in real time while viewing the procedure in real time. It is also possible to conduct the robotic manipulations over the communication channel by an expert in remote location and hence participate in the procedure if it is necessary.

The embodiments of the invention may be described as an exemplary and non-limiting process, which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a procedure, etc.

FIG. 2 is a flow chart of a spatially linked hologram development in real time for procedures as per an embodiment of the invention.

The patient is sedated and placed on a spatially verifiable stage or positioning table (SVPT) that provides three dimensional reference points around the patient that are referenced by the multiple scanning systems to align the collected scan data and hence eliminate displacement errors that are possible when combining the scans from different scanning systems and scans taken at different times. S201.

A scan is taken of the patient encompassing the field of procedure using a high resolution scan unit such as MRI or CT scan. S202.

The high resolution scan data is collected by a processing system and saved in a scan data database in the storage unit of the processing system. S203.

The high resolution scan data is also processed by the processing system to generate high resolution 3-D image data ready for feeding the 3-D image generation system, such as 3-D holographic projectors. The 3-D image data is stored in an image database in the storage unit of the processing system. S204.

The image data is sent to the 3-D image generator to enable the image generator to produce the high resolution 3-D image of the patient. This forms the base image for combining with real time image data for use in the procedures. S205.

An ultra-sonic scanning system with multiple sensors is used to generate the real time scan data from which to produce the real time image data. The scanning sensors are positioned in spatially coordinated manner, with coordinates identified with respect to the available reference points already existing, on and around the patient. These sensors provide optimal scans to collects real time scan data from the field of procedure. S206.

The real time scan data is collected by the processing system in real time and saved in a real time scan database in the storage unit of the processing system. S207.

The real time scan data collected by the processing system is also used to generate real time image data which is also stored in a real time image data base in the storage unit of the processing system. S208.

The real time image data is used by the processor to update the image data available from the high resolution scans on the processing system in real time with spatial alignment and coordination using the reference points set up and referenced during high resolution and ultra-sonic scanning. The reference points enable the image data from the two scans to be integrated in a seamless fashion to produce real time 3-D capable image data of the patient. S209.

The real time updated 3-D capable image data is sent to the 3-D imaging system where it is used by the 3-D imaging system to generate real time continuously updating image of the patient and the instrumentation that are spatially aligned and coordinated in a verifiable way with the patient for display. S210.

The generated spatially coordinated real time 3-D image displayed on the 3-D imaging system is used for visual tracking and execution of the procedures using robotics and other instruments by the experts. S211.

Embodiments of the invention may be a machine-readable medium having stored thereon instructions which program the processor to perform some or all of the operations described above. A machine-readable medium may include any mechanism for storing or transmitting information in a form readable by a machine (e.g., a computer), such as Compact Disc Read-Only Memory (CD-ROMs), Read-Only Memory (ROMs), Random Access Memory (RAM), and Erasable Programmable Read-Only Memory (EPROM). In other embodiments, some of these operations might be performed by specific hardware components that contain hardwired logic. Those operations might alternatively be performed by any combination of programmable computer components and fixed hardware circuit components.

While the invention has been described in terms of several embodiments, those of ordinary skill in the art will recognize that the invention is not limited to the embodiments described, but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

What is claimed is:

1. A method for generation of a real-time image data and enabling a 3-D holographic image of a patient and instruments within the field of a procedure, the method comprising steps of;
    generating high resolution scan data of the field of a procedure with the patient and a set of pre-defined reference points, using a high resolution scanning system;
    processing the high resolution scan data to generate a high resolution image data in an image processing unit;
    generating a real-time scan data of the field of the procedure with the patient and instruments used and the set of pre-defined reference points using a real-time scanning system;
    converting the real-time scan data into real-time image data in the image processing unit;
    combining the high resolution image data with real-time image data using the set of pre-established reference points included within and around the scans to generate a spatially coordinated and updated image data of the patient and the instruments used within the field of procedure in real-time using the processing power of the image processing unit; and
    generating the real-time 3-D holographic image using the updated and spatially coordinated image data.

2. The method of claim 1, wherein the spatially coordinated and updated real-time image data enable generation of a real-time 3-D holographic image, of the patient and the instruments used within the field of procedure, for the surgeon to visually observe the procedure in real time using the 3-D holographic image.

3. The method of claim 2, wherein the real-time 3-D holographic image enable the surgeon to use the real-time visual updates to follow and conduct the procedure with good visibility.

4. The method of claim 1, wherein the availability of image data, for generation of real time 3-D holographic image, enable surgeons to conduct the procedure remotely using robotics using the generated real-time 3-D holographic image.

5. The method of claim 1, wherein the real-time updated 3-D holographic image is used by experts following the procedure from remote locations to provide feedback and advice to the person conducting the procedure also in real time.

6. The method of claim 1, wherein the real-time scanning system used is an ultrasonic scanning system.

7. The method of claim 1, where the high resolution scanning system used is a magnetic resonance imaging (MRI) system.

8. The method of claim 1, wherein the high resolution scanning system is one of a X-Ray, Computer Tomography (CT), Position emission tomography (PET) and nuclear medical imaging (NMI) system.

9. A 3-D imaging system for generation and display of a 3-D image of a field of a procedure consisting of a patient, instruments used, and the field of the procedure in real time comprising:
    an image processing system;
    at least a high resolution scanner coupled to the image processing system for generating a high resolution scan of the field of the procedure with the patient and the pre-defined reference points;
    at least a real-time scanner coupled to the image processing system for generating a real-time scan of the field of the procedure with the instrumentation used and the pre-defined reference points; and
    at least a 3-D image generator coupled to the image processing system;
        wherein the image processing system collects the high resolution scan data generated with the patient and the field of procedure on a verifiable reference generation unit with pre-defined reference points encompassing the field of procedure and processes the high resolution scan data to generate a high resolution image data of the field of the procedure with the patient and the set of pre-defined reference points, which is up dated by the image processing system using real time image data, generated from the real-time scan of the field of the procedure including the patient and the instruments used for the procedure on the a verifiable reference generation unit with the same pre-defined reference points encompassing the field of procedure by the real-time scanner, with spatial coordination and alignment established by use of the alignment of the pre-defined reference points within the high resolution image data and the real-time image data during real-time update of the image data by the image processing system, to produce a real-time updated image data of the field of procedure with the patient and the instruments used with spatial coordination and alignment, which real-time updated image data is provided to the 3-D image generator by the image processing system to generate a 3-D image of the field of a procedure consisting of a patient, instruments used, and the field of the procedure in real-time.

10. The 3-D imaging system of claim 9, wherein the 3-D imaging system is communicably connected to the internet for sending the real-time image data to experts at remote sites enabling them to generate 3-D image of the procedure in real-time for monitoring and providing advice to the individual conducting the procedure and further participate in the procedure in real-time.

* * * * *